(12) United States Patent
Kovalenko et al.

(10) Patent No.: US 7,982,874 B2
(45) Date of Patent: Jul. 19, 2011

(54) METHOD AND APPARATUS FOR MEASURING PARTICLE SIZES IN A LIQUID FIELD OF THE INVENTION

(75) Inventors: Konstantin Vasilievich Kovalenko, Moscow (RU); Svetlana Vladimirovna Krivokhizha, Moscow (RU); Leonid Leonidovich Chaikov, Moscow (RU)

(73) Assignee: P.N. Lebedev Physical Institute of The Russian Academy of Science (RU)

( * ) Notice: Subject to any disclaimer, the term of this patent is extended or adjusted under 35 U.S.C. 154(b) by 207 days.

(21) Appl. No.: 12/274,060

(22) Filed: Nov. 19, 2008

(65) Prior Publication Data
US 2009/0213372 A1 Aug. 27, 2009

(30) Foreign Application Priority Data
Nov. 20, 2007 (RU) ................................ 2007142525

(51) Int. Cl.
*G01N 15/02* (2006.01)
(52) U.S. Cl. ...................................................... 356/336
(58) Field of Classification Search ........... 356/335–343
See application file for complete search history.

(56) References Cited

U.S. PATENT DOCUMENTS

| | | | |
|---|---|---|---|
| 4,975,237 A | 12/1990 | Watling | |
| 4,983,040 A | 1/1991 | Chu et al. | |
| 5,155,549 A | 10/1992 | Dhadwal | |
| 5,402,508 A | 3/1995 | O'Rourke et al. | |
| 5,646,597 A | 7/1997 | Hamburger et al. | |
| 5,693,944 A | 12/1997 | Rich | |
| 5,815,611 A | 9/1998 | Dhadwal | |
| 5,818,583 A * | 10/1998 | Sevick-Muraca et al. | 356/336 |
| 5,822,072 A | 10/1998 | Dai et al. | |
| 5,973,779 A * | 10/1999 | Ansari et al. | 356/301 |
| 6,016,195 A | 1/2000 | Peters | |
| 6,469,787 B1 | 10/2002 | Meyer et al. | |

(Continued)

FOREIGN PATENT DOCUMENTS
DE 19725211 C1 6/1998
(Continued)

OTHER PUBLICATIONS

Photon Correlation and Light Beat Spectroscopy. Ed. by H. Z. Cummins, E.R. Pike, Plenum Press, New York—London, 1974. Translation. Ed. by G. Cumming and E. Pike, Mir, Moscow, 1978.

(Continued)

*Primary Examiner* — Michael P Stafira
*Assistant Examiner* — Isiaka O Akanbi
(74) *Attorney, Agent, or Firm* — Amster, Rothstein & Ebenstein LLP

(57) ABSTRACT

A method of measuring sizes of particles suspended in a liquid using optical mixing spectroscopy of scattered light and an apparatus for implementing the method are disclosed. The method involves making measurements by a fiber optic probe introduced into a medium under investigation, the probe including several multiple or single mode optical fibers. One of the optical fibers transmits light into the medium, while the other optical fibers transmits scattered light to a device for providing spatial coherence of the light and then to a light detector. Auxiliary optical fibers are used to determine the relationship between spectral line widths of multiple and single light scattering when measurements are conducted in very turbid media and for determining particle sizes from multiple rather than single scattering spectrum.

2 Claims, 3 Drawing Sheets

U.S. PATENT DOCUMENTS

| | | | |
|---|---|---|---|
| 6,519,032 B1 * | 2/2003 | Kuebler et al. | 356/337 |
| 6,819,420 B2 * | 11/2004 | Kuebler et al. | 356/337 |
| 6,958,816 B1 | 10/2005 | Dogariu et al. | |
| 7,187,441 B1 * | 3/2007 | Sevick-Muraca et al. | 356/336 |
| 7,236,250 B2 | 6/2007 | Iwai et al. | |

FOREIGN PATENT DOCUMENTS

| | | |
|---|---|---|
| GB | 220265 | 1/1990 |
| RU | 2306970 | 12/2006 |

OTHER PUBLICATIONS

In-Line Particle Size Measurements for Cement and Other Abrasive Process Environments, by A.P. Malcolmson, J.J. Holve. Proc. of IEEE/PCA 40th Cement Industry Technical Conference, Rapid City, South Dakota, 1998.

Great Britain Patent Office Search Report, dated Nov. 24, 1998 for Appln. No. GB9818345.2.

* cited by examiner

METHOD AND APPARATUS FOR MEASURING PARTICLE SIZES IN A LIQUID

CROSS-REFERENCE TO RELATED APPLICATIONS

This application claims priority to Russian Application No. RU 2007142525, filed Nov. 20, 2007.

FIELD OF THE INVENTION

The invention relates to processes for measuring and controlling particle sizes in micro- and nanoemulsions, colloidal solutions and suspensions of particles in liquids and gases. The invention is applicable in chemical processes, in particular, in petrochemistry, food and medical industries, medical research, for producing nanoparticles for electronic and electrical industry, controlling the state of operating fluids in mechanical and power engineering, i.e. for controlling processes of producing or using colloidal solutions, emulsions and suspensions of solid or liquid particles.

BACKGROUND OF THE INVENTION

A method of measuring particle sizes from the scattered light spectrum using the optical mixing spectroscopy [1] is currently used worldwide and in Russia [2]. FIG. 1 shows a conventional optical arrangement for measuring particle sizes by optical mixing spectroscopy techniques, where 1 is an argon, He—Ne or semiconductor laser; 2—polarizers; 3—objectives or lenses; 5—an emulsion cell; Θ—the scattering angle; 4—an aperture diaphragm; 8—a diaphragm in front of a light detector; 9—a light detector; 10—a correlator or spectrum analyzer; 6—a homo- or heterodyning beam; 7—a diaphragm.

A focused beam of a laser 1 propagates through a polarizer 2, a focusing lens 3, a cell 5 with a sample under investigation, and the light scattered at angle Θ is provided to a light detector 9 by an objective 3 which creates, on a light detector cathode, an image of the laser beam in the cell. A small scattered volume is cut out from the beam by the image of diaphragm 8 and bounded by the laser beam diameter and the image of diaphragm 8 on the beam. An auxiliary reference laser beam 6 at the same frequency or frequency-shifted may be introduced in the scheme to provide optical homodyning or heterodyning.

Beats of light frequency components give rise to intensity fluctuations in a square-law light detector, the fluctuations repeating themselves in the detector current and being analyzed by a correlator or spectrum analyzer. Spectrum of the light scattered by monodisperse particles has a Lorentzian shape with halfwidth Γ, and the time correlation function of the field of such light is exponent. The correlator analyzes the photocurrent that repeats the light intensity, rather than the light field. The intensity correlation function is an exponent with a decay rate 2Γ on a "substrate" of noncoherent background. At ideal spatial coherence of the light field, the amplitude of the correlation function exponent is equal to the background [1]. The spectrum analyzer or correlator determines spectral scattering line width Γ or correlation function coherence time $\tau_c = 1/\Gamma$, and particle radius r is calculated therefrom:

$$\Gamma = q^2 D \qquad (1)$$
$$= \frac{KT}{6\pi\eta r} q^2$$

or $$r = \frac{KT}{6\pi\eta\Gamma} \left( \frac{4\pi n}{\lambda} \sin\frac{\Theta}{2} \right)^2$$

where q is the scattering vector $\vec{q} = \vec{K}_s - \vec{K}_L$, $\vec{K}_s$, $\vec{K}_L$ are wave vectors of the scattered and incident light, $$|q| = \frac{4\pi n}{\lambda} \sin\frac{\Theta}{2},$$

n is the refractive index of the medium; λ is the wavelength of incident light; Γ is the scattering angle; K is the Boltzmann constant; T is the absolute temperature; η is the shear viscosity; D is the diffusion coefficient of particles.

Where a suspension or emulsion includes particles of several sizes the time correlation function is a sum of several exponents whose amplitudes are proportional to squared intensity of light scattering on particles of respective size. In this case, spectrum is the Lorentzian sum.

The important point is that to conduct spectral or correlation analysis of intensity beats, the light entering at the light detector must be spatially coherent, otherwise the intensity beats at various small areas of the light detector will be out of phase and compensate each other, this making the analysis thereof impossible. In the conventional arrangement, the spatial coherence conditions are attained owing to the use of a small source (scattering volume) with efficient diameter $d_s$ and the inclusion, in the optical scheme, of a small aperture diaphragm 7 (FIG. 1) having diameter $d_a$. For the source and a round diaphragm, the condition of presence of spatial coherence (or, as is generally referred to, detection of a single coherence area) is expressed by formula [1]:

$$d_a d_s \leq \frac{1.22 \lambda L}{\pi} \approx \frac{\lambda L}{2.57} \qquad (2)$$

where L is the distance between the source and the aperture diaphragm.

Practical application of the conventional arrangement for particle sizing in industry is prevented by the necessity to place a sample into a special optical cell, and due to the presence of dust and coarse aggregate formations both in raw stock and products.

The former problem has been partially solved (only for pipelines!) in Great Britain through the provision of a quite complex bypass line including a kind of an optical cell [3]. The situation is still worse with the problem of dust.

First, coarse dust particles scatter light more intensely than fine colloid particles of interest. Measurements are possible only due to a high concentration of the particles measured, but distortions are still present. To overcome this effect, complex mathematical processing of correlation functions and separation of the resulting exponents by Tikhonov regularization methods can be employed. However, the impact of dust on the measurement results is not restricted by the additional scattering only.

In a conventional optical arrangement, the scattering volume is defined by intersection between an exciting laser beam (Ø~0.2 mm) and a photomultiplier field of view (Ø~0.2 mm at $d_s=d_a$) and amounts to $V_{sc}\approx 0.8 \cdot 10^{-5}$ cm.

The so small scattering volume either contains a few dust particles or is completely free of them. For this reason, first, the intensity fluctuations of dust-scattered light have a non-Gaussian statistics, and the size distribution of all particles, including the dust ones, cannot be determined from the resulting correlation function (or spectrum). Second and even more important, with such statistics of dust-scattered light the background constant component of the resulting correlation function changes; exponent expansion of monotonically decreasing portion of the function becomes inadequate, so the results even may have nothing to do with sizes of actually important particles and define only sizes of dust particles and the relationship between the concentration thereof and the scattering volume.

And finally, in many cases nanoemulsions and particularly microemulsions used in industry are virtually opaque due to strong light scattering, so to measure particle sizes therein the sample should be placed in a special thin (about 5÷100 μm) flat cell, this making real-time measurements and on-line process control impracticable.

Methods of using, in light scattering spectroscopy, fiber optic probes that are placed directly in the medium under investigation are disclosed in [4,5]. But these devices fail to measure correlation functions of scattered light because an optical fiber per se doesn't provide spatial coherence conditions. It is precisely this fact that caused failures of first attempts to use optical fibers for investigating narrow spectral lines of scattered light and measuring particle sizes therefrom.

Improvements in the conventional optical arrangement with optical fibers were initially reduced to the use of a conventional optical system; the optical fiber only transmitted the exciting light from a laser to a cell and/or from an aperture diaphragm to a light detector [6,7]. Then optical fiber "testers" (a kind of a probe) have appeared comprising a lens between the "tester" and the scattering volume [8,9] or an integrated optics at fiber ends [10,11] or both [12]. In [11] it is implicitly suggested that spatial coherence conditions should be provided by the use of single mode optical fibers. In [10] spatial coherence conditions are attained by intersection of a light beam with a small diameter field of view. [12] does not deal with this issue. In an apparatus disclosed in [13] for measurements in turbid media, light is introduced into the volume under investigation, and scattered light is output through the same single mode optical fiber; and a "coupler" (a device for beams-sharpening in a single optical fiber and dividing the light from the single optical fiber between several ones) is used. Multiple scattering should be eliminated in [13] by the use of a light source with a short coherence length.

Most closely related to the present invention is a method and an apparatus for measuring particle sizes in a liquid by optical mixing spectroscopy technique using optical fibers in the presence of multiple light scattering, as disclosed in [14]. The method comprises introducing light from a low coherence source into a volume under investigation and outputting scattered light through the same single mode optical fiber, and using a "coupler" (means for beams-sharpening in a single optical fiber and dividing the light from the single optical fiber between several ones), in which the source light is added to the scattered light for further heterodyning thereof. It is supposed that spatial coherence conditions are observed owing to the use of single mode optical fibers. Multiple scattering should be eliminated by the use of a light source with a short coherence length. This supposedly enables the correlation function of light scattered in a small volume only to be obtained using heterodyning.

The prior art method has the following disadvantages: due to the use of a small coherence volume, light that enters the light detector from the remaining volume of the fiber field of view, even if does not produce a correlation function distorted by multiple scattering, generates an enormous noncoherent background. Then, first, the correlation function will have an extremely small amplitude as compared to the background (hence a low precision), and second, due to a small efficient coherent scattering volume, when dust particles are present, the correlation function background will be distorted due to non-Gaussian statistics thereof and this will give rise to errors in the obtained correlation function processing, so measurements of particle radii in turbid media are impracticable. In addition, the obligatory application of single mode fibers involves a complicated adjustment of the system and its sensitivity to mechanical disturbances.

The present invention is aimed to:

extend functionality owing to the ability of measurements in turbid media in which multiple light scattering is present;

improve precision, reliability and immunity to interference (from dust) of particle size measurements in micro- and nanoemulsions, colloidal solutions and suspensions of particles in actual industrial conditions, without the need for placing the sample into a special cell and for special adjustment;

provide tolerance to mechanical disturbances.

SUMMARY OF THE INVENTION

The aims of the invention are attained in a method for measuring particle sizes in a liquid by optical mixing spectroscopy of particle-scattered light, consisting in illuminating a scattering volume by a laser and collecting the scattered light by optical fibers. The scattered light is collected by a primary and auxiliary multimode optical fibers that are parallel to an illuminating multimode fiber. Spatial coherence of the scattered light is provided at output ends of the collecting fibers in front of a light detector. Particle size r is determined by relationship:

$$r = \left(\frac{r_{aux}}{r_{pr}^2}A + \frac{B}{r_{pr}}\right)^{-1},$$

where $r_{pr}$, $r_{aux}$ are the particle radii obtained by primary and auxiliary collecting multimode optical fibers, respectively; A and B are values of universal dependence of normalized particle radius $r_{pr}/r$ on $r_{aux}/r_{pr}$ ratio.

A method in accordance with the invention is implemented in an apparatus comprising fiber optic probes; a laser conjugated with an input end of an illuminating optical fiber and a light detector arranged at an output end of the collecting optical fiber. The probe further comprises one or more collecting multimode optical fibers that are parallel to the illuminating optical fiber. The primary collecting optical fiber is in immediate proximity of the illuminating optical fiber, while the remaining collecting optical fibers are some distance away from the illuminating optical fiber. Endfaces of all optical fibers are jointly polished to form an input end of the probe. A scattered light coherence area selection system is arranged between output ends of the collecting optical fibers and the light detector.

BRIEF DESCRIPTION OF THE DRAWINGS

The above and related objects, features and advantages of the present invention will be more fully understood with reference to the following detailed description of the preferred, albeit illustrative, embodiments of the present invention when considered in conjunction with the accompanying figures, wherein.

DESCRIPTION OF THE PREFERRED EMBODIMENTS

Figure 1:
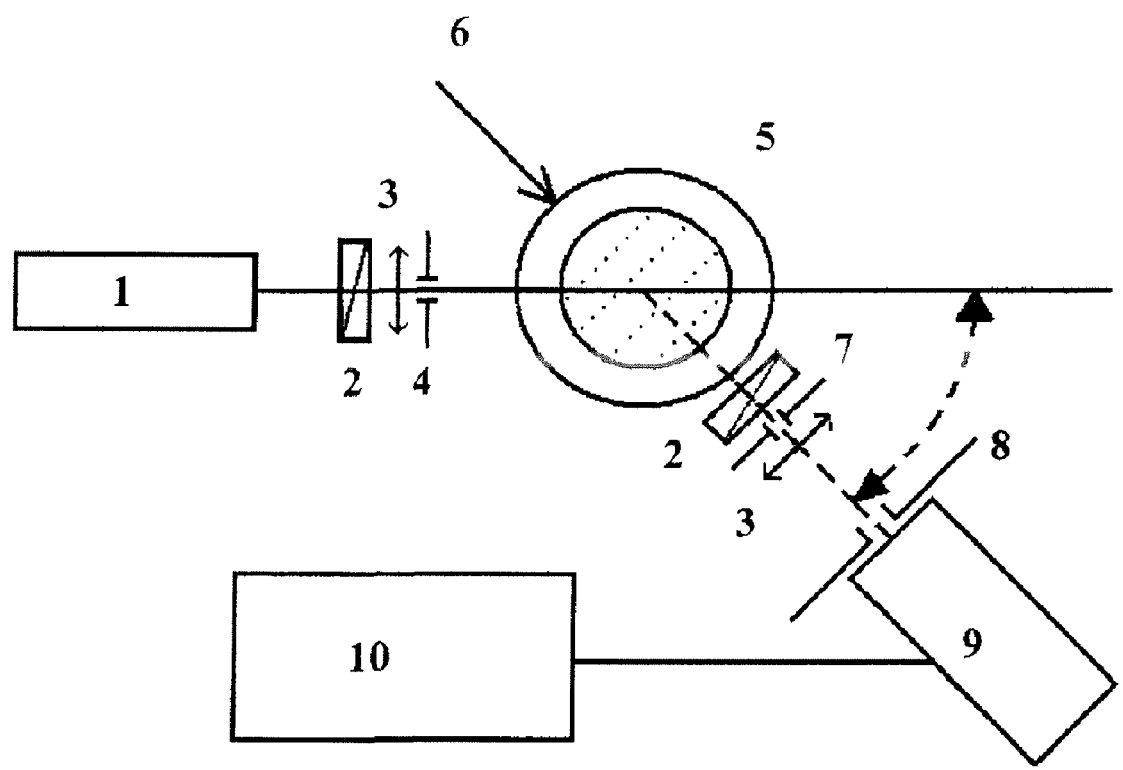
FIG. 1 shows a conventional optical arrangement for measuring particle sizes by optical mixing spectroscopy techniques.
Figure 2:
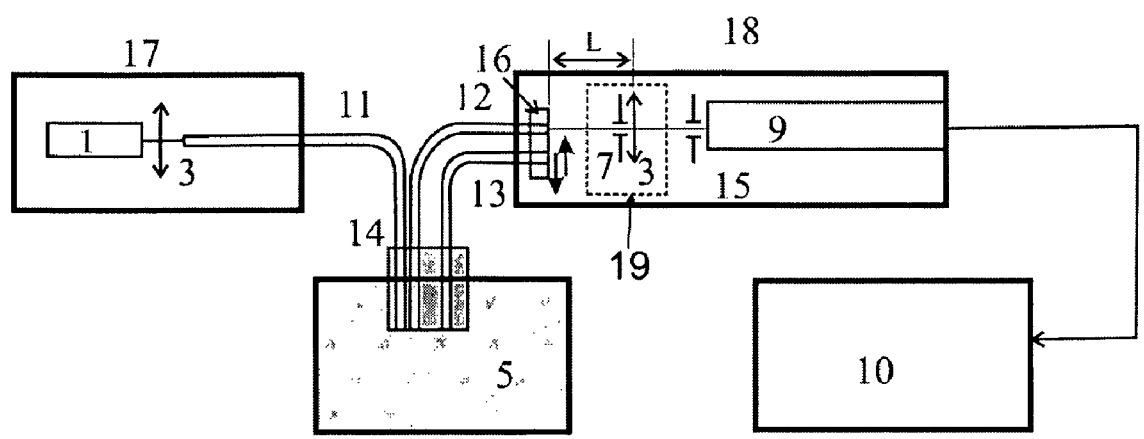
FIG. 2 shows a schematic diagram of an apparatus for implementing a method in accordance with the present invention.

FIG. 2 shows a schematic diagram of an apparatus for implementing a method in accordance with the present invention, the apparatus comprising: a laser 1, a laser-optical fiber interface 17, an illuminating fiber 11; an fiber optic probe 14; a reservoir 5 with a suspension or emulsion under investigation; a primary collecting optical fiber 12; an auxiliary collecting optical fiber 13; a collecting fiber-light detector interface 18; a displacing coupling 16; distance L between a fiber output end and an aperture diaphragm; an aperture diaphragm 7; an objective or lens 3; a cathode diaphragm 15; a light detector 9; a correlator or spectrum analyzer 10; a coherence area selection system 19.

The present method is implemented by the apparatus in the following manner. An optical fiber output end is embedded in a thin probe 14 of cylindrical or another convenient shape along with an input end of a collecting multimode fiber 12. The step of embedding is provided such that the fibers 11 and 12 should be parallel and in immediate vicinity from each other so that side surfaces thereof contact each other. Working surfaces of the optical fibers are jointly polished. The resulting three-fiber probe 14 is placed into a volume 5 with a suspension under investigation (colloidal solution, emulsion, etc.). Light emitted from the fiber 11 illuminates the investigated medium volume in a cone shape with angular opening a≈15° for a conventional optical fiber having the core diameter of about 100 μm. Light back-scattered from particles (more precisely, at scattering angle θ=178-180°) enters the collecting fiber 12 and is directed to a square-law light detector 9 that is mounted together with output ends of fibers 12 and 13, lens 3 and diaphragms 7,15 in a collecting fiber-light detector interface 18. A coherence area selection system 19 includes a lens 3 and a diaphragm 7.

Then, spectral scattering line width Γ is determined using optical mixing spectroscopy of scattered light, and radius r of particles is determined therefrom using (1). Scattering volume is defined by the intersection between the first fiber illuminated volume and the second fiber field of view, and reaches $0.7 \cdot 10^{-2}$ cm²; this immediately overcomes the problem of non-Gaussian statistics of dust scattering owing to the increased scattering volume, and solves the task of protection against the dust effect.

Light source is an endface of the fiber 12 (typically, with $d_s$≈100 μm diameter). To reduce exposure, an additional diaphragm is mounted on the light detector cathode, the diaphragm size should be not less than the fiber endface image on the light detector cathode. The aperture diaphragm diameter is defined using relationship (2) to obtain a single coherence area. In practice, an aperture diaphragm 7 having $d_a$=0.9 mm at L=10 cm is sufficient to obtain 30% coherence ratio (correlation function amplitude/0.30 background ratio). Particle sizes of a diluted latex solution, measured in a test tube by the invented method and by a conventional method agree, within the limits of error (1.5%), with each other and with the certified value of latex sphere radius, 100±2 nm.

Where the invented apparatus is used to make measurements in very turbid media, such as milk or emulsion, emulsol EMU-1 (liquid lubricant-coolant), the correlator detects the correlation function of multiple scattered light, rather than that of a single scattered one, for which relationship (1) is true. In this case the correlation function has near-exponential shape, but its width may differ from that of the correlation function of a single-scattered light several times. The difference depends on photon path length l in the medium or extinction ratio σ (σ=l/l). σ and l are explicitly related with scattering coefficient R and scattering ratio.

To obtain information about values σ and l and the relation between single and multiple scattering line widths, an end of one or more auxiliary fibers 13 is inserted in the probe end some distance away (typically 0.5-1.5 mm) from and parallel to the illuminating and collecting fibers (FIG. 2). Fibers ends are jointly polished in a single plane. Output ends of optical fibers 12,13, and so on, are secured in an optical fiber-light detector interface in a laterally moving coupling (16 in FIG. 2) to enable light measurements in any one of the optical fibers. Use of a diaphragm 15 in front of the light detector cathode is obligatory in this case since it is necessary to alternately measure light output from the collecting and auxiliary optical fibers. Relationship between single and multiple scattering line widths is determined based on the relation of intensities and spectral line widths in collecting, $I_{pr}$, $\Gamma_{pr}$, and auxiliary, $I_{aux}$, $\Gamma_{aux}$, fibers, and the respective coefficient is introduced in the result obtained from formula (1). Distance between centers of the optical fibers 11 and 12 is 0.27 mm, and between centers of the optical fibers 11 and 13 is 1.1 mm.

Figure 3:
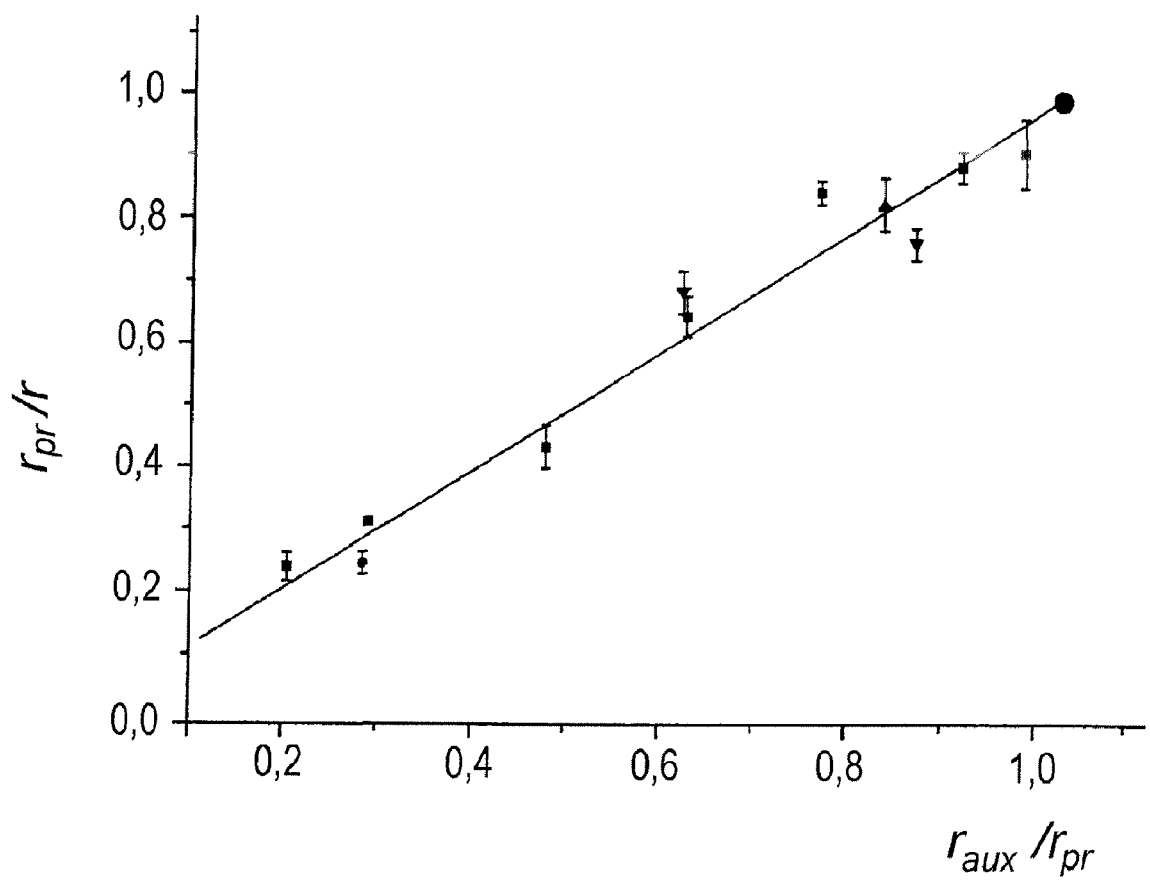
FIG. 3 shows a universal dependence of normalize particle radius $r_{pr}/r$ on $r_{aux}/r_{pr}$ ratio (take off the /r on $r_{aux}$ take off the /$r_{pr}$ take off the subscript again ratio).

FIG. 3 shows a universal dependence of normalized particle radius $r_{pr}/r$ on $r_{aux}/r_{pr}$ ratio. Emulsions: ■ EMU-1, diluted to 10%, r=118.4 nm; ▼ TAFOL, diluted to 5%, r=83.38 nm; ▲ latex, r=103.6 nm; ● EMU-1, concentration 5.5%, r=118.3 nm. Big round point on the top right side of the plot corresponds to the case of infinite dilution and absence of multiple scattering, where $r_{aux}=r_{pr}-r$.

This dependence is universal for particles of various radii and different materials, but it changes with variation in distances between the collecting, illuminating and auxiliary optical fibers, so it should be determined for each probe individually. Values A and B in the dependence are approximated from the measured data by formula:

$$\frac{r_{pr}}{r} = A\frac{r_{aux}}{r_{pr}} + B$$

For the probe used in the investigations A=0.971±0.019, B=0.029±0.019.

Therefore, with a fiber optic probe made as disclosed in the description and a universal dependence of $r_{pr}/r$ on $r_{aux}/r_{pr}$ ratio determined for the probe, true particle size r can be obtained from $r_{aux}$ and $r_{pr}$ values measured in the collecting and auxiliary fibers both in transparent and turbid emulsions and suspensions using formula:

$$r = \left(\frac{r_{aux}}{r_{pr}^2}A + \frac{B}{r_{pr}}\right)^{-1}$$

A measurement method in accordance with the invention makes it possible to dispense with special optical cells. A fiber optic probe can be placed in a reservoir of any size, a pipeline, etc., where the need for particle measurement exists. The optical system associated with a sample doesn't require alignment, and the coherence area selection system can be adjusted and fixed before starting the apparatus service.

Measurements can be conducted both in transparent and very turbid media, such as milk or 5-10% colloidal solution of emulsol (liquid lubricant-coolant, LLC). In this case correlation function of multiple, rather than single light scattering is determined, whose coherence time $\Gamma_m$ is related with coefficient $\Gamma$ defined on the basis of line width/intensity ratios in collecting and auxiliary fibers (fibers 12 and 13 in FIG. 2).

Owing to selection of a greater coherence area, a method in accordance with the invention is immune to dust present in a sample.

REFERENCES CITED

1. Photon correlation and light beating spectroscopy. Ed. by H. Z. Cummins, E. R. Pike, Plenum Press, New York—London, 1974. Translation. Ed. by G. Cumming and E. Pike, Mir, Moscow, 1978.
2. Kovalenko K. V., Krivohizha S. V., Rakaeva G. V., Chaikov L. L., Method and apparatus for preparing colloidal solutions, RU No. 2306970 of 21 Dec. 2006.
3. Malcolmson A. P., Holve D. J. In-line particle size measurements for cement and other abrasive process environments. Proc. Of IEEE/PCA 40$^{th}$ Cement Industry Technical Conference, Rapid City, S. Dak., 1998 (attached).
4. O'Rourke P. E., Livingston R. R. Fiber optic probe having fibers width endfaces formed for improved coupling efficiency and method using same. U.S. Pat. No. 5,402,508 Mar. 28, 1995.
5. Dai Sh., Young J. P. Fiber optic probe and system for spectral measurements. U.S. Pat. No. 5,822,072 Oct. 13, 1998.
6. Broun R. G. W. Dynamic light scattering apparatus. U.S. Pat. No. 4,975,237, Dec. 4, 1990.
7. Chu B., Dhadwal H. S. Light scattering and spectroscopic detector. U.S. Pat. No. 4,983,040, Jan. 8, 1991.
8. Ansari R. R., Suh K. I. Fiber-optic imaging probe. U.S. Pat. No. 5,973,779, Oct. 26, 199.
9. Meyer W. V., Camel D. S., Smart A. E. Dynamic light scattering homodyne probe. U.S. Pat. No. 6,469,787 B1, Oct. 22, 2002.
10. Dhadwal H. S. Method and apparatus for determining the physical properties of materials using dynamic light scattering techniques. U.S. Pat. No. 5,155,549, Oct. 13, 1992.
11. Dhadwal H. S. Method and apparatus for submicroscopic particle sizing, and probe therefore. U.S. Pat. No. 5,815,611, Sep. 29, 1998.
12. Keil und Kollegen. Faserdetektor zur Detektion des Streulichtes oder des Fluoreszenzlichtes einer flussigen Suspension. Germany Patent No DE 19725211 C1, Jun. 4, 1998.
13. Iwai T., Ishii K. Dynamic light scattering measurement apparatus using phase modulation interference method. U.S. Pat. No. 7,236,250 B2, Jun. 26, 2007.
14. Dogariu A., Poiescu G., Rajagopalan R. Microrheology methods and systems using low-coherence dynamic light scattering. U.S. Pat. No. 6,958,816 B1, Oct. 25, 2005.

The invention claimed is:

1. A method of measuring sizes of particles in a liquid, comprising:
   illuminating a scattering volume with an illuminating multimode optical fiber;
   collecting the multiple and single scattered light by a primary collecting multimode optical fiber and one or more auxiliary collecting multimode optical fibers, all of the illuminating, primary collecting and auxiliary collecting multimode optical fibers being arranged parallel to each other;
   detecting the multiple and single scattered light by a light detector;
   providing spatial coherence condition for the multiple and single scattered light at output ends of the primary collecting multimode optical fiber and the one or more auxiliary collecting multimode fibers in front of the light detector; and
   determining particle sizes using optical mixing spectroscopy of scattered light, where particle size r is determined from relationship:

$$r = \left(\frac{r_{aux}}{r_{pr}^2}A + \frac{B}{r_{pr}}\right)^{-1}$$

where $r_{pr}$, $r_{aux}$ are particle radii obtained as assumed for single scattering by the primary and auxiliary collecting multimode optical fibers, respectively; A and B are values of universal dependence of normalized particle radius $r_{pr}/r$ on $r_{aux}/r_{pr}$ ratio.

2. An apparatus for measuring sizes of particles in a liquid, comprising:
   fiber optic probe;
   a laser conjugated with an input end of an illuminating multimode optical fiber;
   a primary collecting multimode optical fiber;
   one or more auxiliary collecting multimode optical fibers;
   a light detector; and
   a scattered light coherence area selection system mounted between output ends of the primary collecting multimode optical fiber, the one or more auxiliary collecting multimode optical fibers and the light detector, the scattered light coherence area selection system being adapted to provide the spatial coherence condition for the multiple and single scattered light at output ends of the primary collecting multimode optical fiber and the one or more auxiliary collecting multimode fibers in front of the light detector;
   a correlator or spectrum analyzer for determining particle sizes using optical mixing spectroscopy of scattered light, where particle size r is determined from relationship;

$$r = \left(\frac{r_{aux}}{r_{pr}^2}A + \frac{B}{r_{pr}}\right)^{-1}$$

where $r_{pr}$, $r_{aux}$ are particle radii obtained as assumed for single scattering by the primary and auxiliary collecting multimode optical fibers, respectively; A and B are values of universal dependence of normalized particle radius $r_{pr}/r$ on $r_{aux}/r_{pr}$ ratio;

all of the illuminating, primary collecting and auxiliary collecting multimode optical fibers being arranged parallel to each other in the probe,
the primary collecting multimode optical fiber being in immediate proximity to the illuminating multimode fiber, and the one or more auxiliary collecting multimode optical fibers being at some distance away from the illuminating multimode fiber, endfaces of all multimode optical fibers being jointly polished to form an input end of the probe.

* * * * *